(12) United States Patent
Appenrodt et al.

(10) Patent No.: US 11,298,528 B2
(45) Date of Patent: Apr. 12, 2022

(54) METHOD AND APPARATUS FOR REPLACING LEAD EXTENSION WITHOUT TUNNELING

(71) Applicant: MEDTRONIC, INC., Minneapolis, MN (US)

(72) Inventors: Peter Appenrodt, Bremen (DE); Daniel Schmitz, Guadalajara (MX); Paul Van Venrooij, Hoensbroek (NL)

(73) Assignee: Medtronic, Inc., Minneapolis, MN (US)

(*) Notice: Subject to any disclaimer, the term of this patent is extended or adjusted under 35 U.S.C. 154(b) by 94 days.

(21) Appl. No.: 15/962,566

(22) Filed: Apr. 25, 2018

(65) Prior Publication Data

US 2018/0272119 A1 Sep. 27, 2018

Related U.S. Application Data

(62) Division of application No. 13/991,783, filed as application No. PCT/US2011/063951 on Dec. 8, 2011, now Pat. No. 9,968,775.

(60) Provisional application No. 61/421,258, filed on Dec. 9, 2010.

(51) Int. Cl.
    *A61N 1/05* (2006.01)
(52) U.S. Cl.
    CPC ..................... *A61N 1/05* (2013.01)
(58) Field of Classification Search
    CPC ....................................................... A61N 1/05
    See application file for complete search history.

(56) References Cited

U.S. PATENT DOCUMENTS

| | | | |
|---|---|---|---|
| 6,605,094 B1* | 8/2003 | Mann | A61B 17/3401 606/129 |
| 8,088,138 B2* | 1/2012 | Pandey | A61B 17/06109 606/190 |
| 8,926,646 B2* | 1/2015 | Pandey | A61B 17/32 606/190 |
| 2005/0171509 A1* | 8/2005 | Hector | A61N 1/3752 604/533 |
| 2007/0050005 A1* | 3/2007 | Lauro | A61N 1/05 607/126 |
| 2008/0103407 A1* | 5/2008 | Bolea | A61N 1/3606 600/529 |
| 2008/0147168 A1 | 6/2008 | Ransbury | |
| 2010/0042169 A1* | 2/2010 | Barker | A61N 1/3752 607/2 |

FOREIGN PATENT DOCUMENTS

WO    WO 2007/127997 A2    11/2007

OTHER PUBLICATIONS

PCT International Search Report and Written Opinion dated May 10, 2012 for PCT/US2011/063951.

* cited by examiner

*Primary Examiner* — Sarah A Simpson
(74) *Attorney, Agent, or Firm* — Mueting Raasch Group

(57) ABSTRACT

Tether apparatus may be used to replace an implanted lead extension with a replacement lead extension without tunneling or the use of tunneling tools.

9 Claims, 20 Drawing Sheets

METHOD AND APPARATUS FOR REPLACING LEAD EXTENSION WITHOUT TUNNELING

RELATED APPLICATIONS

This is a divisional application of U.S. patent application Ser. No. 13/991,783, filed Aug. 13, 2013, now issued as U.S. Pat. No. 9,968,775 on May 15, 2018, which is a U.S. National Stage Application of International Application No. PCT/US2011/063951, filed Dec. 8, 2011, which was published in English on Jun. 14, 2012 as International Patent Publication WO 2012/078875 A1. International Application No. PCT/US2011/063951 also claims priority to U.S. Application No. 61/421,258, filed Dec. 9, 2010.

FIELD

This disclosure relates, inter alia, to implantable medical devices. More particularly, it relates to implantable medical devices and systems employing lead extensions and replacement of implanted lead extensions with new lead extensions.

BACKGROUND

Replacement of lead extensions may be required in a number of situations, such as when there is damage to the extension or upgrading to a new platform that the old extension does not support. Whatever the reason for replacing a lead extension, the process may be difficult.

Current methods to replace a lead extension typically include removing the implanted extension, tunneling a subcutaneous path from a location in proximity to a lead to a location in proximity of an implanted active electrical device, feeding the new extension through the tunneled path, and operably coupling the new extension to the implanted lead and the implanted active electrical device. Sometimes the distance of the tunneled path is long and intermediate cuts may be required to remove the lead extension.

SUMMARY

The present disclosure describes, among other things, methods and apparatus that provide for replacement of a lead extension without tunneling.

In an embodiment, a method for replacing a first implanted lead extension in a subject with a second lead extension includes uncoupling the first implanted lead extension from (i) the implanted lead and (ii) the implanted electrical medical device. The method further includes securing the second lead extension relative to the first implanted lead extension; and withdrawing the first implanted lead extension from the patient through a path to cause the second lead extension to be drawn into the tunneled path while the first implanted lead extension is withdrawn.

In an embodiment, a method for replacing a first implanted lead extension in a subject with a second lead extension includes uncoupling the first implanted lead extension from (i) the implanted lead and (ii) the implanted electrical medical device. The method further includes securing the first lead extension to a tether; and withdrawing the first implanted lead extension from the patient through a path to cause the tether to be drawn into the tunneled path in a first direction while the first implanted lead extension is withdrawn. The method also includes securing the second lead extension to the tether; and withdrawing the tether from the patient through the path in a second direction generally opposite to the first direction to cause the second lead extension to be drawn into the tunneled path in a first direction while the first implanted lead extension is withdraw.

In an embodiment, a tether includes a receptacle configured to receive and secure a free end portion of a lead extension; and an elongate body extending from the receptacle. Such a tether may be used in methods for replacing lead extensions without tunneling or use of tunneling tools as described herein.

By providing tethers, kits, systems, and methods that allow for lead extensions to be replaced without tunneling, injury and other complications sometimes associated with lead extension replacement may be reduced, and time and cost of performing lead extension replacement procedures may also be reduced. These and other advantages will be readily understood from the following detailed description when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure describes, among other things, methods and apparatus that provide for replacement of a lead extension without tunneling. The apparatus and methods described herein may be used in replacing nearly any implanted lead extension that is used to couple a lead to an active implantable electrical medical device. As used within this disclosure, "apparatus" can have either a singular or plural meaning.

Figure 1:
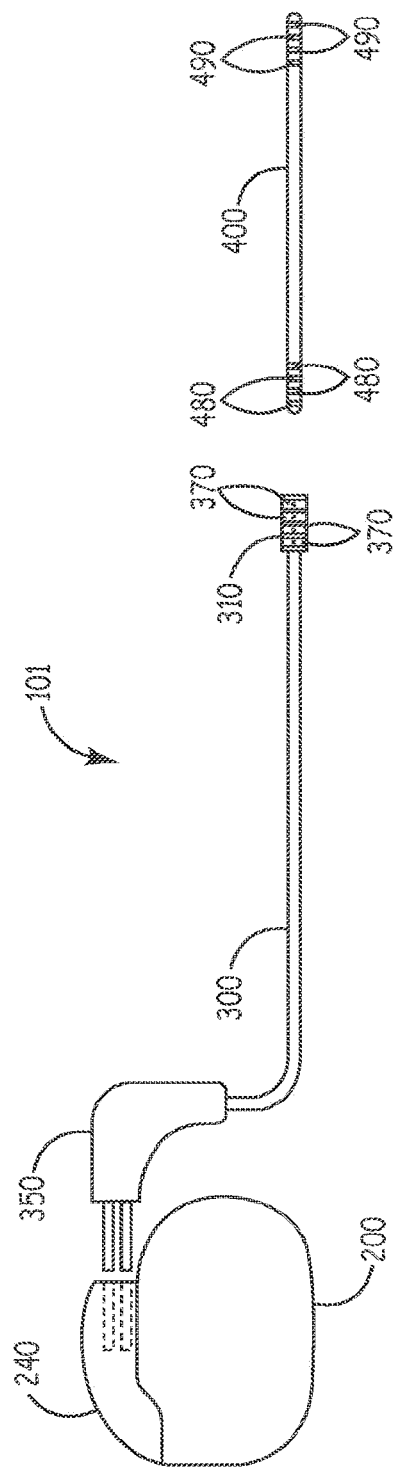
FIG. 1 is a schematic side view of a system including a lead extension for operably coupling a lead to an active implantable electrical medical device.

Referring to FIG. 1, a schematic view of an exemplary embodiment of an implantable active electrical system 101 is shown. In the system shown in FIG. 1, implantable active electrical device 200 includes a connector header 240 configured to receive male connector 350 at proximal end of lead extension 300. Of course, it is understood that device 200 need not have a separate header 240 to receive extension 300. The distal end of extension 300 includes a lead receptacle 310 configured to receive proximal end of lead 400. Receptacle 310 has internal electrical contacts 370 configured to electrically couple extension 300 to lead 400 via electrical contacts 480 disposed on the proximal end portion of lead 400. Electrodes 490 are disposed on distal end portion of lead 400 and are electrically coupled to electrical contacts 480, typically through internal conductors (not shown). Lead 400 may include any number of electrodes 490, e.g. one, two, three, four, five, six, seven, eight, sixteen, thirty-two, or sixty-four. Typically, each electrode 490 is electrically coupled to a discrete electrical contact 480. While not shown, it will be understood that lead 400 may be directly coupled to active implantable medical device 200 without use of extension 300 or adaptor in some systems 101, and that the apparatus and methods disclosed herein can also be used where a lead replacement is required, but no extension is present or used.

Lead extensions of any suitable system employing a lead extension for operably coupling a lead to an active implantable electrical medical device may be replaced in accordance with the teachings presented herein. For example, a lead extension may be associated with an active implantable medical device, such as a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like.

Figure 2:
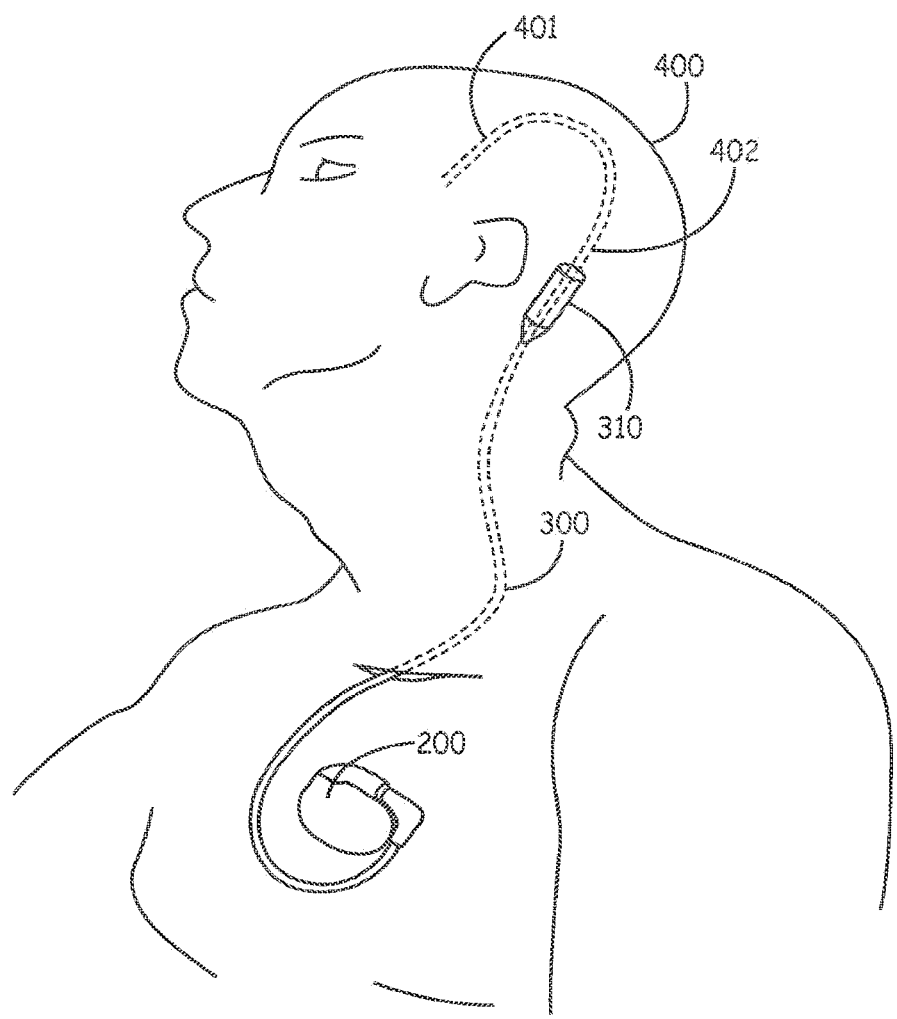
FIG. 2 is a schematic drawing of a system implanted in a patient, where the system includes a lead, a lead extension, and an active implantable electrical medical device.

By way of example and referring to FIG. 2, one type of system where an extension is used is with a deep brain stimulation (DBS) system, which is depicted as implanted in a patient. For DBS, an implantable pulse generator (IPG) 200 is typically placed in the abdominal region of patient or in the pectoral region (as shown). Of course, the IPG 200 may be placed in any medically acceptable location of the patient. The distal end 401 of the lead 400 containing electrodes is placed at a desired location in the patient's brain. The proximal end 402 of the lead 400 is inserted into a receptacle 310 of the lead extension 300, which is connected to the IPG 200. Thus, the lead extension 300 couples the lead 400 to the IPG 200. IPG 200 is capable of generating electrical signals that may be applied to tissue of patient via the electrodes for therapeutic or diagnostic purposes. It will be understood that a lead 400, lead extension 300 or system may be used for purposes of applying electrical signals to tissue of a patient or for sensing signals from tissue of a patient.

Implantation of the lead extension 300 requires tunneling from a location in proximity to the location of the proximal end of the lead 400 to a location in proximity to the implanted location of the IPG 200, which includes tunneling through the neck. A tunneling tool is used to create a subcutaneous path between the implanted location of the IPG 200 to the implanted location of the proximal end of the lead 400, and the extension 300 is fed through the tunneled path. Current methods for replacing lead extensions include such tunneling procedures.

Following are described various exemplary embodiments of methods and apparatus that may be used to replace an implanted lead extension without tunneling or use of a tunneling tool. In many of the described embodiments, a tether is employed in the tunnel-less replacement process. For the purposes of convenience and brevity, many of the processes and tethering apparatus will be described in the context of replacement of a lead extension in a DBS system. However, it will be understood that the tether apparatus and methods described herein may be employed with regard to replacement of a lead extension in nearly any implanted system in which a lead extension is used to couple a lead to an active electrical implantable medical device.

Figure 3A:
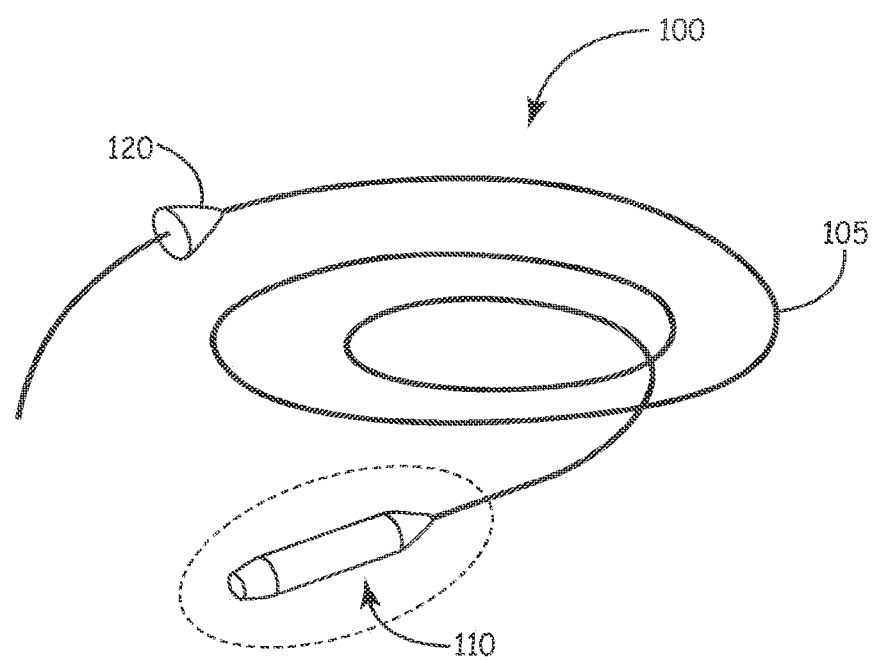
FIG. 3A is a schematic perspective view of a tether apparatus that may be used to replace a lead extension without tunneling or the use of tunneling tools.
Figure 3B:
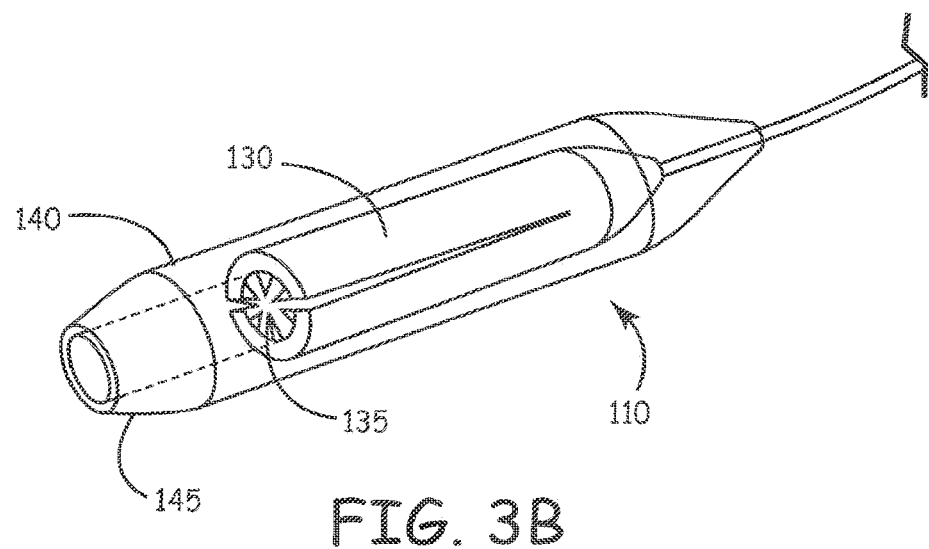
FIG. 3B is a close-up view of an embodiment of the portion of the tether depicted in the dashed line of FIG. 3A.

Referring now to FIGS. 3A-B, an exemplary embodiment of a tether 100 is depicted. FIG. 3B is an enlarged view of an embodiment of the receptacle 110 identified in the dashed line in FIG. 3A. The tether 100 includes a receptacle 110 configured to receive and secure a free end portion of a lead extension and an elongate body 105 extending from the receptacle 110. The depicted tether 100 also includes a tapered element 120 disposed about the elongate body 105 in proximity to the distal end of the elongate body. The tapered element 120 is disposed about the elongate body 105 such that the portion with the smaller diametric dimension faces the receptacle 110 when the tether 100 is pulled through a patient.

The free end of the lead extension may be inserted in and secured relative to the receptacle 110 in any suitable manner. For example, set screws, such as those used to secure a lead in a lead extension receptacle may be used, or, for example, a collet, a clamp, a spring or the like may be employed. A variety of connectors that may be readily modified to be advantageously employed with a tether receptacle 110 include connectors as described in U.S. Patent Publication No. 2005/0143714, entitled "Sutureless Pump Connector", published Jun. 30, 2005, filed on Sep. 27, 2004 as U.S. patent application Ser. No. 10/950,727 and naming Michael Hegland, et al. as inventors. One of skill in the art will appreciate that it may be advantageous to ensure that an overly sufficient amount of surface contact occurs between the attachment mechanism of the receptacle 110 and the lead extension to ensure a robust connection that can withstand pulling forces within ranges that may be encountered with regard to the methods described herein.

With reference to the embodiment shown in FIG. 3B, the tether receptacle 110 may include an outer sleeve 140 defining a lumen housing an interior clamp 130. The clamp may include one or more resiliently deflectable arms having engagement means, such as, for example, teeth 135 depicted to grippingly engage a free end portion of a lead extension. Thus the opening of the clamp 130 in the depicted embodiment is configured to receive the free end portion of a lead extension, and as the lead extension is forced further into the clamp 130, the clamp 130 more securely engages the lead extension. The teeth 135 may extend a distance within the clamp 130, with greater length of the teeth 135 resulting in greater surface area of the contact between the lead extension and the clamp and a more aggressive connection. Of course, as discussed above, any suitable engagement means, such as, for example, a clamp, may be employed for securely engaging the lead extension.

As shown in FIGS. 3A-B, the receptacle 110 of the tether 100 preferably includes a contoured front portion 145, such as, for example, a taper that will facilitate pulling the tether 100 through a patient, as will be more evident when discussed with regard to FIG. 4 below. The front face of the receptacle 110, as well as other portions of the receptacle 110, preferably has an outer diametric dimension that is less than, equal to, or not substantially greater than the outer diameter of the body of the lead extension that the receptacle 110 is configured to receive. This is because scar tissue may have developed around the lead extension, and pulling a larger diameter object through scar tissue can require a more force. Because large forces may be applied, it is important, but not essential, that the connection between the receptacle 110 and the lead extension be robust or that the receptacle 110 or other portions of the tether 100 are designed to reduce required pulling forces.

An exemplary embodiment of a procedure for using a tether 100, such as the one depicted in FIG. 3, to replace a lead extension is illustrated in FIGS. 4A-I. In the method depicted in FIGS. 4A-I, numerical references in parentheses refer to particular steps, which are described in more detail herein. One of ordinary skill in the art will appreciate that the steps can be varied to suit the particular application.

Figure 4A:
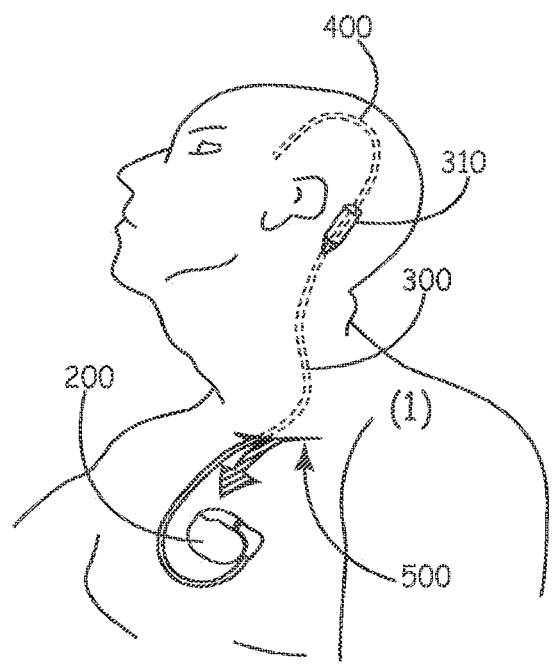
FIGS. 4A-J are schematic drawings illustrating a method for replacing a lead extension without tunneling, using a tether as depicted in FIG. 3A.

At step (1) an incision 500 is made in proximity to the location of the implanted active electrical medical device 200 The active medical electrical medical device 200 and a proximal portion of the attached lead extension 300 is explanted through the incision 500 (see FIG. 4A).

Figure 4B:
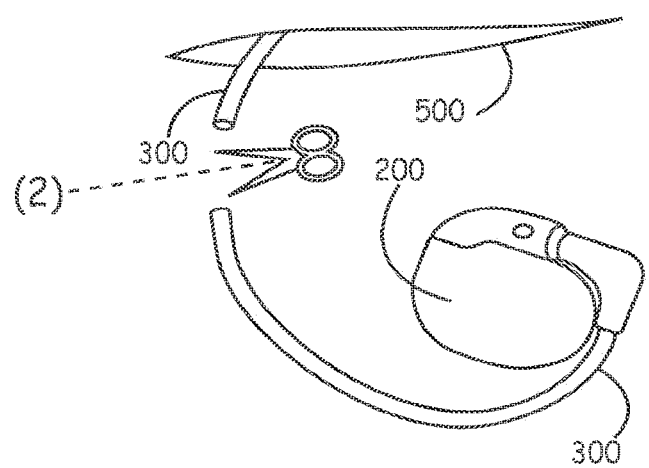

At step (2) the extension 300 is removed, for example, by cutting, from the active device 200, providing a free end of the extension 300 external to or accessible through the incision 500 (see FIG. 4B).

Figure 4C:
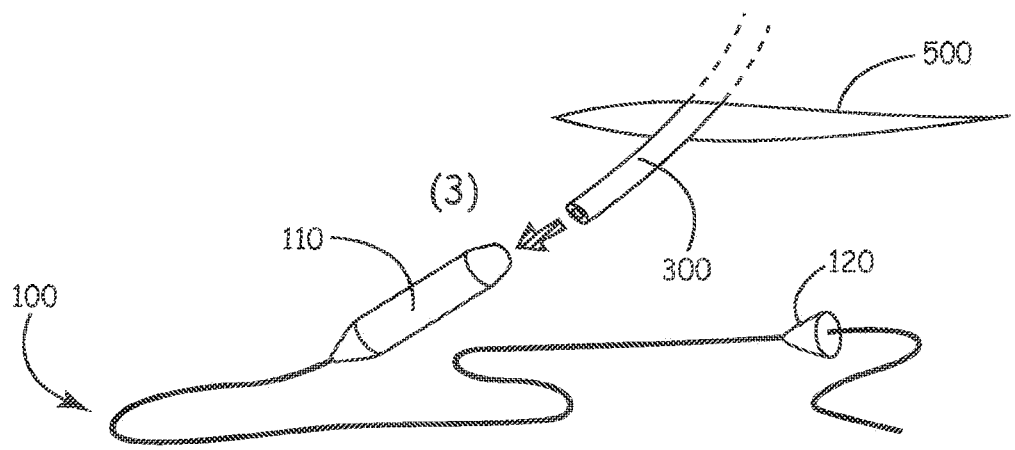

At step (3) the free end of the lead extension 300 extending or accessible through the incision 500 is secured in the receptacle 110 of the tether 100 (see FIG. 4C).

Figure 4D:
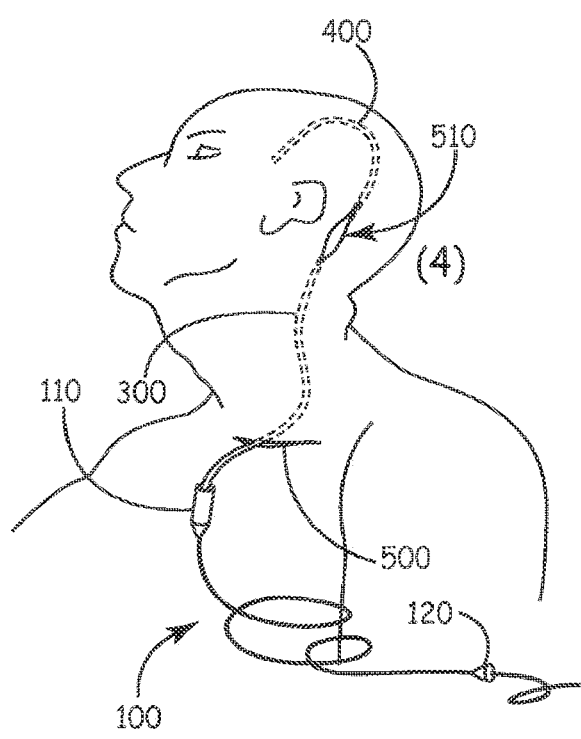

At step (4), a second incision 510 is made in proximity to the location of the lead receptacle of the lead extension 300 (see FIG. 4D).

Figure 4E:
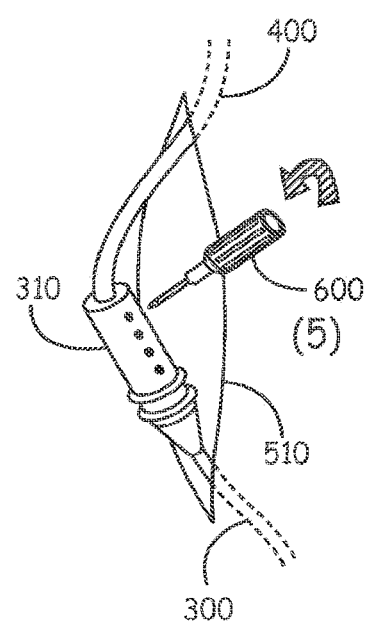

At step (5), the lead 400 is disconnected from the lead extension 300 by removal of the lead 400 from the lead receptacle 310 (see FIG. 4E). If required or helpful, any suitable tool 600, such as the screw driver depicted in FIG. 4E, may be used to facilitate disconnection of the lead 400 from the lead extension 300.

Figure 4F:
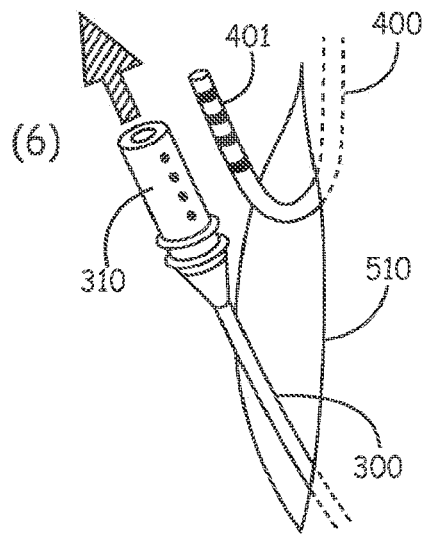

At step (6), the extension 300 is pulled through the incision 510 to pull the tether through the subcutaneous path previously occupied by the extension 300 (see FIG. 4F). As should be understood from the disclosure, this method leaves the lead 400 implanted in the patient.

Figure 4G:
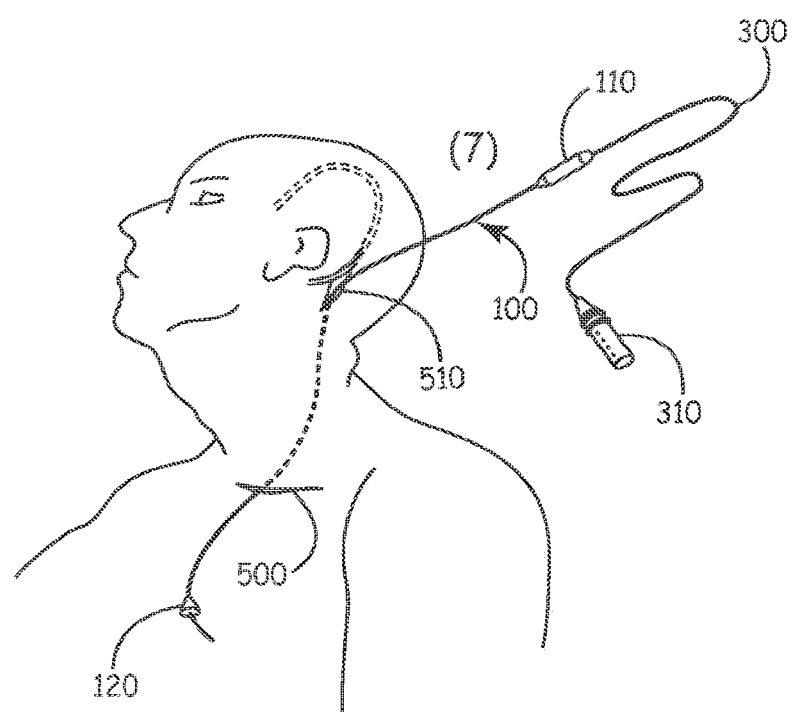

At step (7), the remainder of the lead extension 300 is pulled from the patient until a proximal portion of the tether 100 (the portion that includes the receptacle 110) is exposed through the incision 510 (see FIG. 4G).

Figure 4H:
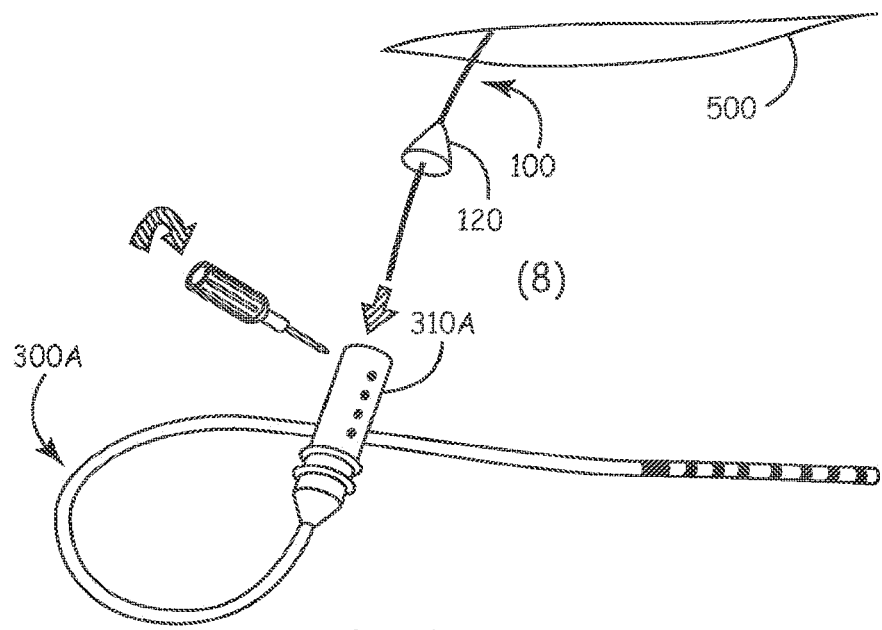

At step (8), a distal portion of the tether 100 remaining external to the first incision 500 is secured within a lead receptacle 310A of the replacement extension 300A (see FIG. 4H). Accordingly, the distal portion of the tether 100 is configured and dimensioned to be received by and secured within the lead receptacle 310A of the replacement extension 300. Further, the elongate body of the tether 100 is sufficiently long to extend through the subcutaneous path from and beyond the first 500 and second 510 incisions. As shown in FIG. 4H, a tool 600, such as the depicted screwdriver, may be employed to assist in securing the tether 100 within the receptacle 310A.

Figure 4I:
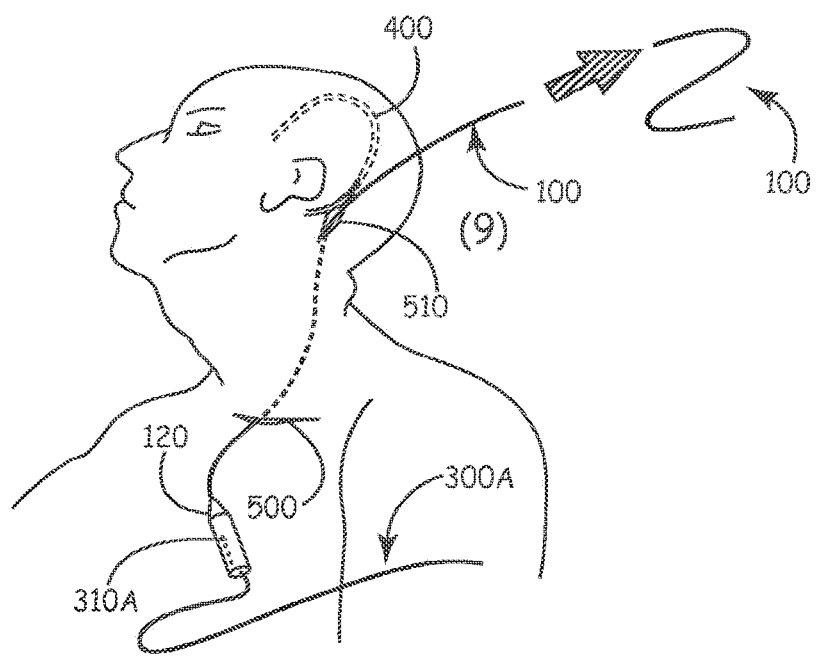

At step (9), the tether 100 is pulled from the patient through the second incision 510, drawing the replacement extension 300A through the subcutaneous path previously occupied by the originally implanted extension (see FIG. 4I). As shown in the embodiment depicted in FIG. 4I, the tether 100 is secured to the distal end of replacement extension 300A. This is accomplished by insertion of a portion of the replacement extension into the lead receptacle 310. The tapered element 120 abuts against or is located near the housing of the receptacle to facilitate pulling the replacement extension 300A through the patient.

Figure 4J:
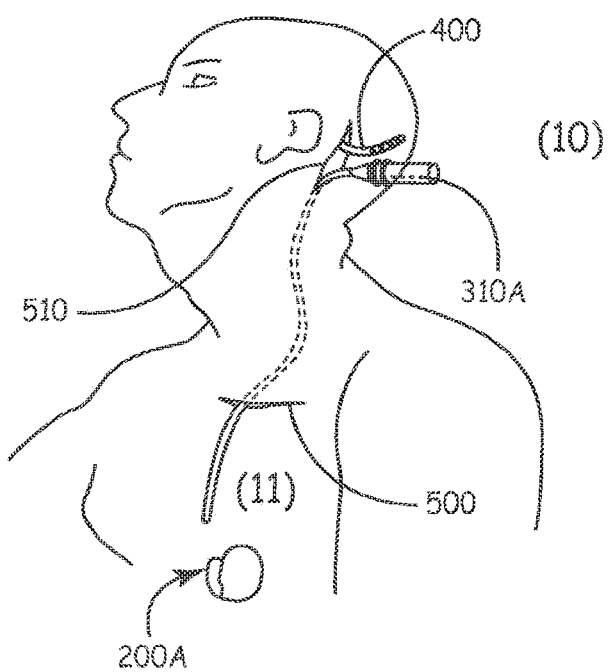

At step (10), the lead 400 is connected to and secured within the lead receptacle 310A of the replacement lead extension 300 which has been pulled through the patient a sufficient distance to provide access to the lead receptacle 310A through the incision 510 (see FIG. 4J).

At step (11), the replacement extension 300 is connected to an active implantable medical device 200, which may also be a replacement device (see FIG. 4J). The active device 200 and connected portions of the replacement extension 300A may be implanted in the patient through the incision 500. Thus, the lead extension 300 may be replaced with a replacement lead extension 300A without any tunneling or the use of tunneling tools.

Figure 5:
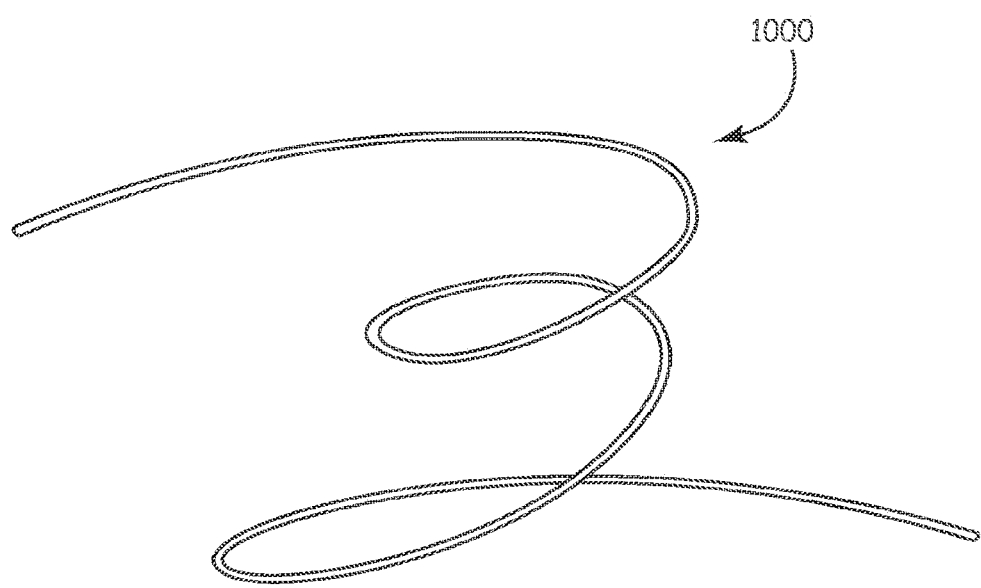
FIG. 5 is a schematic perspective view of a tether apparatus that may be used to replace a lead extension without tunneling or the use of tunneling tools.

Referring now to FIG. 5, a different embodiment of a tether 1000 that may be used to replace a lead extension without tunneling is shown. The depicted tether 1000 consists essentially of an elongate body, such as a cord, wire, tube or the like.

A method for using a tether 1000 depicted in FIG. 5 to replace a lead extension without tunneling is depicted in FIGS. 6A-G. As with FIGS. 4A-I, steps of the method are identified in FIGS. 6A-G with numerical references in parentheses.

Figure 6A:
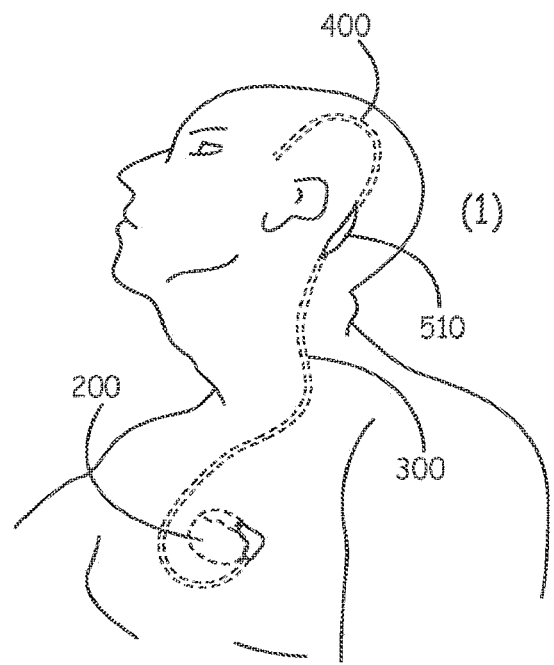
FIGS. 6A-G are schematic drawings illustrating a method for replacing a lead extension without tunneling, using a tether as depicted in FIG. 5.

At step (1), an incision 500 is made in the patient in proximity to the implanted location of the lead receptacle of the lead extension 300 (see FIG. 6A).

Figure 6B:
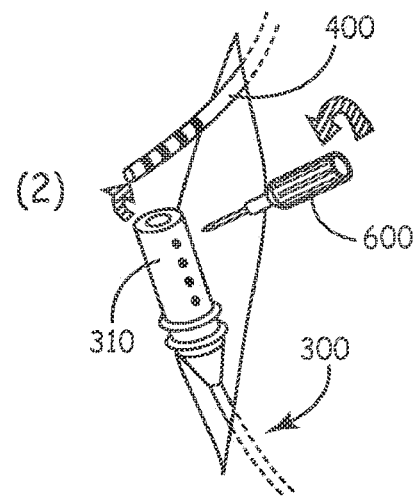

At step (2), the lead 400 is disconnected from the lead extension 300 by removal of the lead 400 from the lead receptacle 310 (see FIG. 6B). Any suitable tool 600, such as the screwdriver depicted in FIG. 6B, may be used to facilitate disconnection of the lead 400 from the lead extension 300.

Figure 6C:
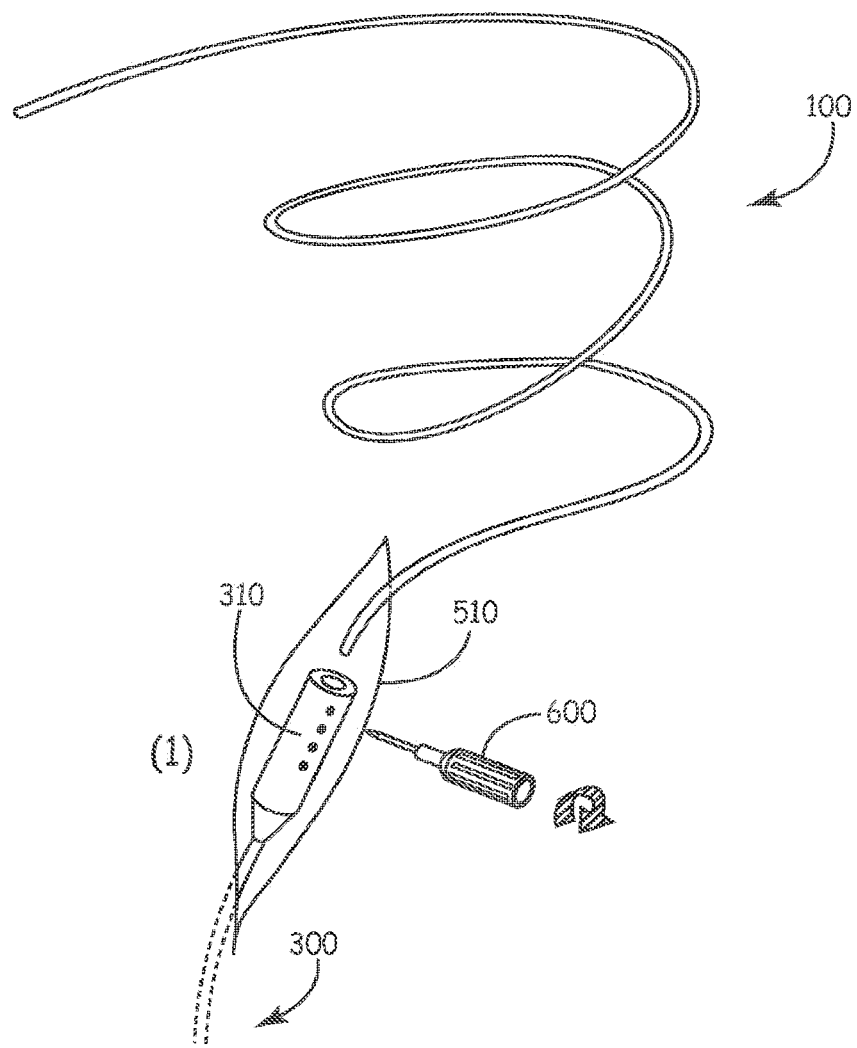

At step (3), a free end of the tether 100 is inserted into and is secured within a lead receptacle 310 of the extension 300 (see FIG. 6C). Accordingly, the free end portion of the tether 100 is configured and dimensioned to be received by and secured within the lead receptacle 310. As shown in FIG. 6C, a tool 600, such as the depicted screwdriver, may be employed to assist in securing the tether 100 within the receptacle 310 (e.g., by tightening set screws).

Figure 6D:
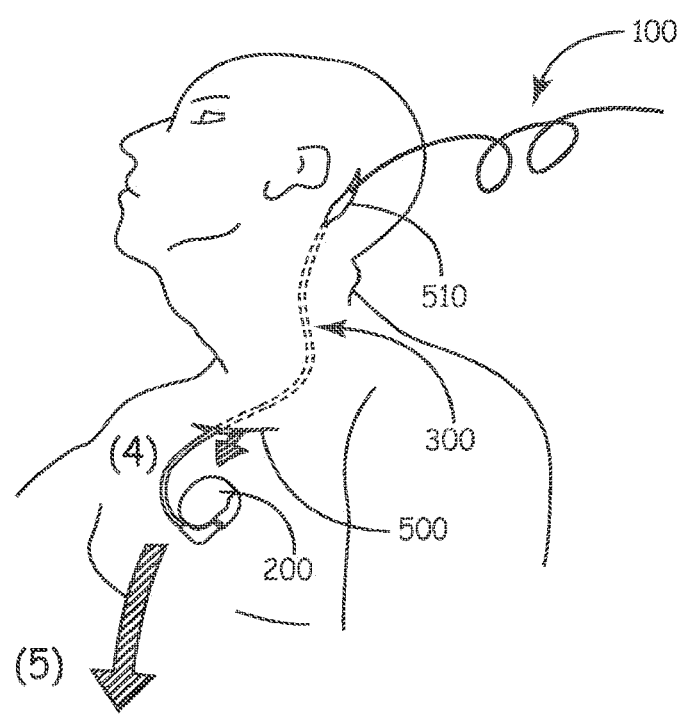

At step (4), an incision 500 is made in proximity to the location of the implanted active electrical device 200 and the device 200 is removed from the patient through the incision 500 (see FIG. 6D). Still with reference to FIG. 6D, the lead extension is then pulled through the incision 500 at step (5), which causes the tether 100 to be pulled through the subcutaneous path previously occupied by the lead extension 300.

Figure 6E:
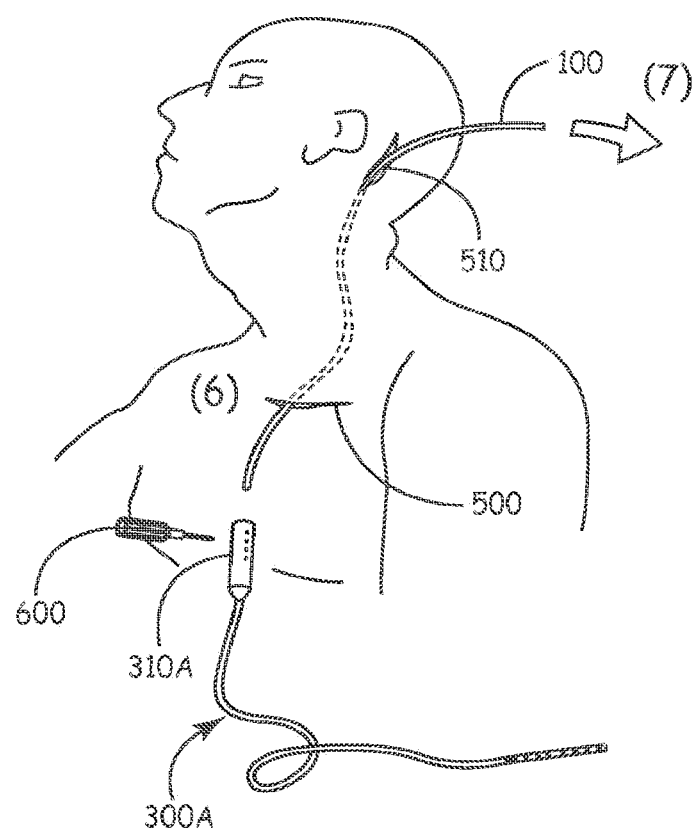

At step (6), a free end portion of the tether 100 that has been pulled through incision 500 is inserted into and secured within a lead receptacle 310A of a replacement extension 300A (see FIG. 6E). As shown in FIG. 6E, a tool 600, such as the depicted screwdriver, may be employed to assist in securing the tether 100 within the receptacle 310A (e.g., by tightening set screws). Accordingly, the free end of the tether 100 is configured and dimensioned to be insertable and securable within the receptacle 310A. Still with reference to FIG. 6E, the tether 100 is pulled through incision 500 causing the replacement extension 300A to be drawn through the subcutaneous path previously occupied by the originally implanted lead extension. Accordingly, the tether 100 is sufficiently long to extend through the subcutaneous path and beyond incisions 500, 510.

Figure 6F:
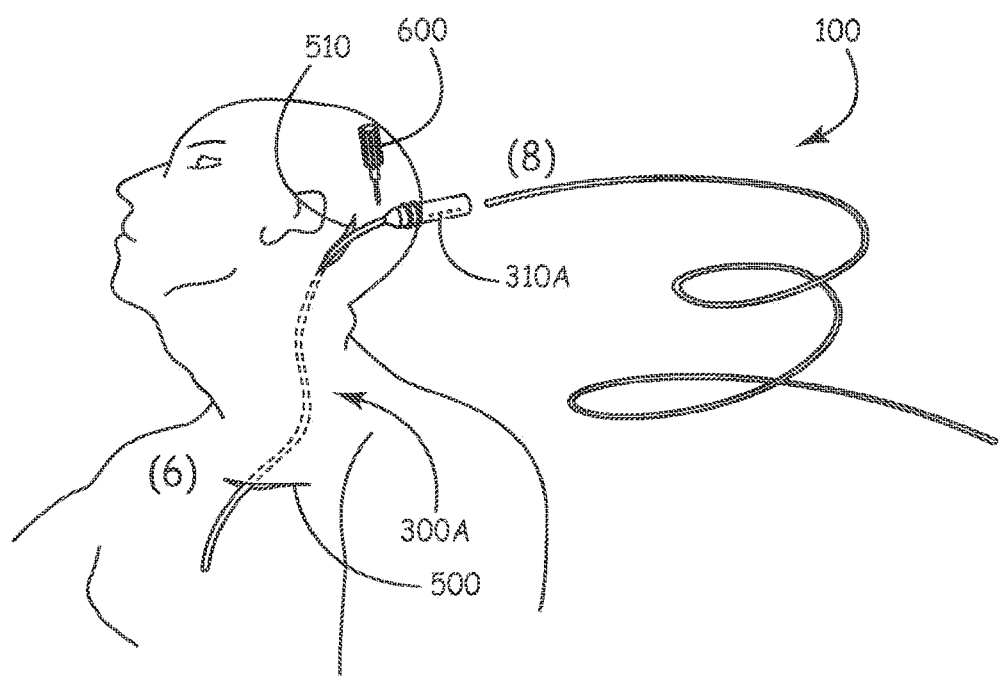

At step (8), the tether 100 is disconnected from the lead receptacle 310A of the replacement extension 300A. As shown in FIG. 6F, a tool 600, such as the depicted screwdriver, may be employed to assist in removing the tether 100 from the receptacle 310 (e.g., by loosening set screws).

Figure 6G:
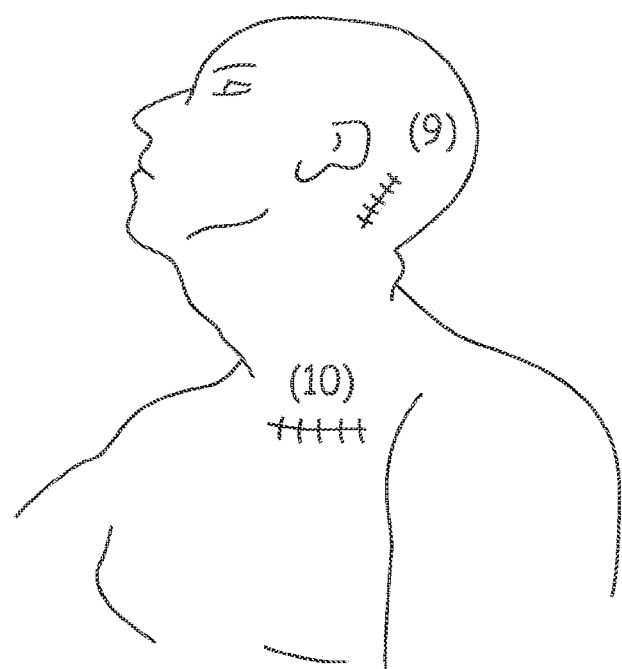

Referring to FIGS. 6F-G, the lead (not shown) may be connected and secured within the receptacle 310A of the replacement extension 300A and the incision 510 may be closed (9). The other end of the replacement extension 300 may be connected to an active medical device (not shown), implanted through incision 500, and the incision 500 may be closed (10). Thus, an implanted lead extension may be replaced without tunneling or use of tunneling tools.

Figure 7:
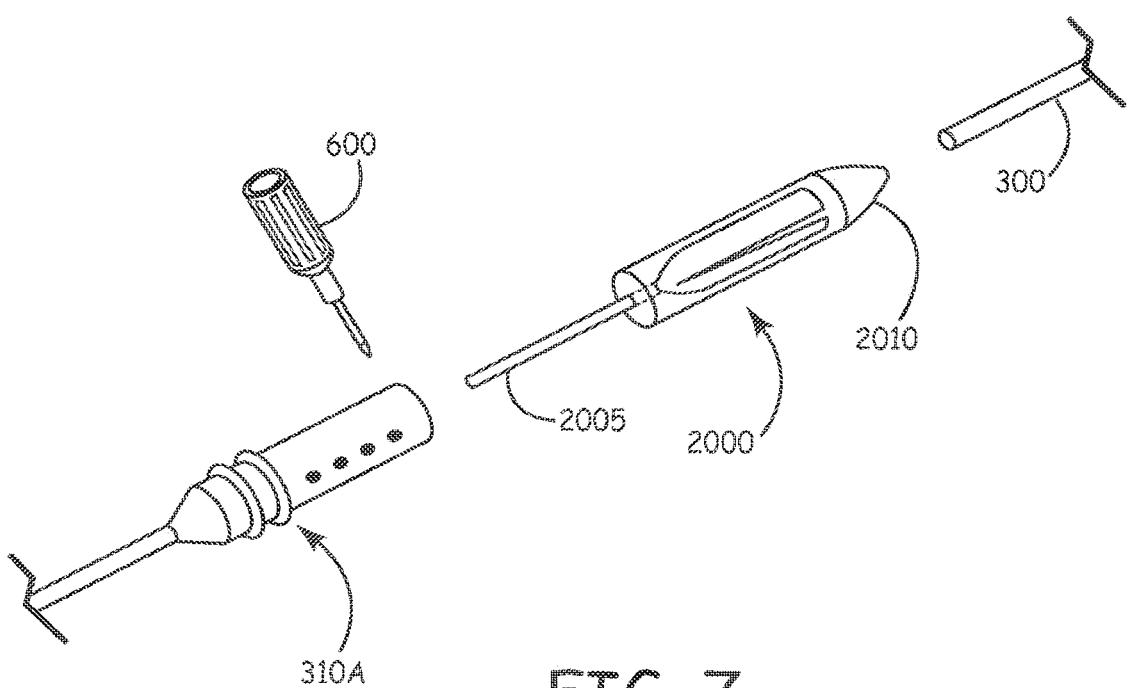
FIG. 7 is a schematic perspective view of an embodiment of a tether and associated portions of a lead extension to be replaced and a replacement lead extension.

Referring now to FIG. 7, an exemplary embodiment of a tether 2000 is shown. The depicted tether 2000 is similar in many respects to the tether shown in FIG. 3. For example, the tether 2000 includes a receptacle 2010 configured to receive and secure a free end portion of a lead extension 300; the receptacle 2010 is tapered; and the elongate body 2005 extends from the receptacle 2010. However, the length of the elongate body 2005 that extends from the receptacle 2010 is shorter that the elongate body of the tether depicted in FIG. 3. The elongate body 2005 is configured to be inserted into and secured within a lead receptacle 310A of a replacement lead extension. The length of the elongate body 2005 may be configured such that the receptacle abuts against or is located near to the housing of the lead receptacle 310A of the replacement extension when inserted in and secured within the lead receptacle 310A. The tether 2000 depicted n FIG. 7 additionally serves as an adapter for securing a lead extension 300 relative to a replacement lead extension.

Figure 8:
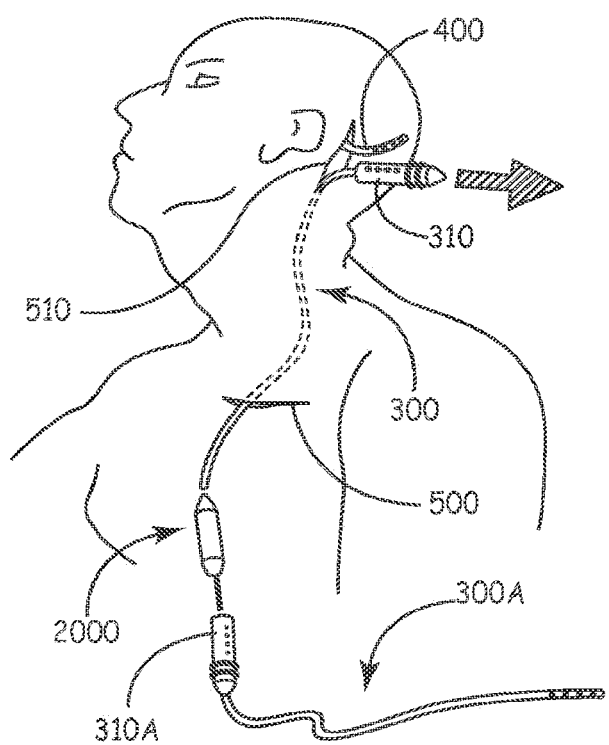
FIGS. 8-9 are schematic drawings illustrating methods for replacing a lead extension without tunneling, using a tether as depicted in FIG. 7.

Referring now to FIG. 8, an exemplary process for using a tether depicted in FIG. 7 is shown. The implanted extension 300, which has a free end extending from or accessible through an incision 500 made in proximity to an implanted location of an active electrical medical device (not shown) that has been removed through incision 500, is inserted and secured within the receptacle of the tether 2000. A free end of the elongate body of the tether 2000 is inserted into and secured within a lead receptacle 310A of the replacement lead extension 300A. An incision 510 is made in proximity to the implanted location of the lead receptacle 310 of the implanted lead extension 300 to be replaced, and the lead 400 is disconnected from the lead receptacle 310. The lead extension 300 is then pulled from the patient through the incision 510, causing the replacement extension 300A to be pulled through the subcutaneous path previously occupied by the originally implanted extension 300.

Figure 9:
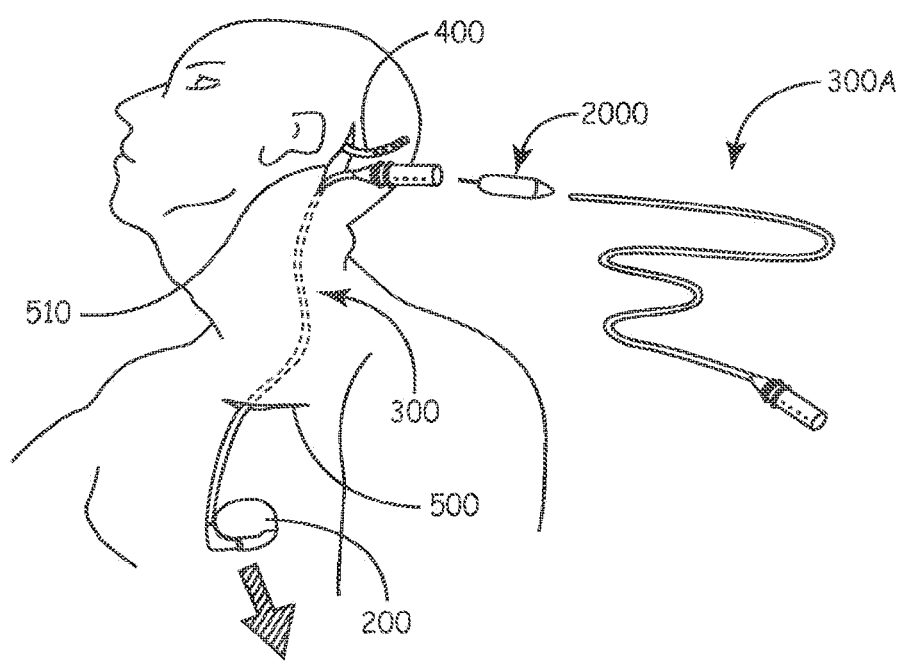

Referring now to FIG. 9, an alternative process for using a tether depicted in FIG. 7 is shown. In the depicted embodiment, an incision 510 is made in proximity to the implanted location of the lead receptacle 310 of the originally implanted lead receptacle 300 to be replaced. The lead 400 is disconnected from the lead receptacle 310, and a free end of the elongate body of the tether 2000 is inserted into and secured within the lead receptacle 310 of the lead extension 300. A free end of the replacement lead extension 300A is inserted into and secured within the receptacle of the tether 2000. The active electrical device 200 and coupled proximal portion of lead extension 300 are removed from the patient via incision 500. The originally implanted lead extension 300 is then pulled from the patient through incision 500 causing the replacement lead extension 300A to be pulled though the subcutaneous path previously occupied by the originally implanted lead extension 300.

Figure 10:
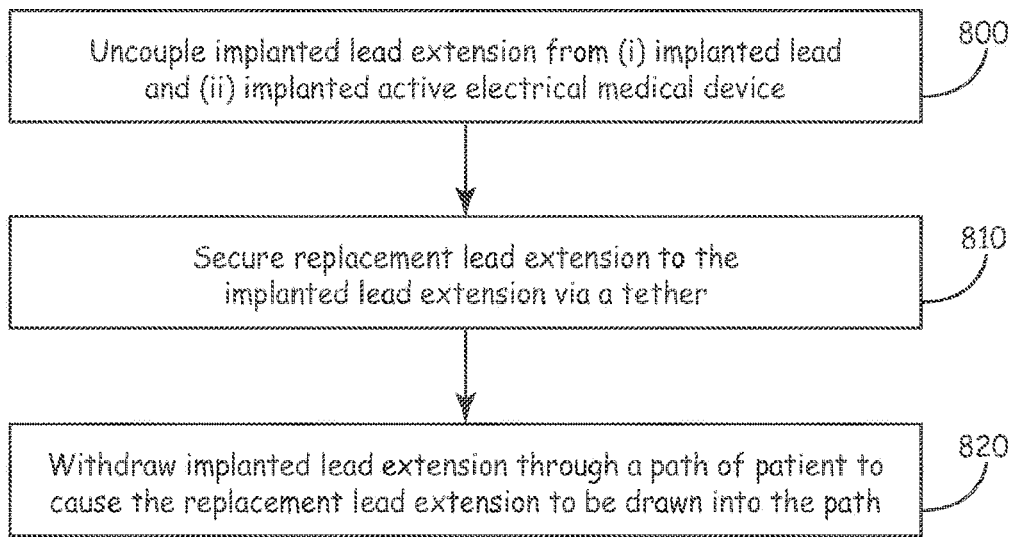
FIGS. 10-11 are flow diagrams of overviews of methods for replacing a lead extension without tunneling or use of tunneling tools.
Figure 11:
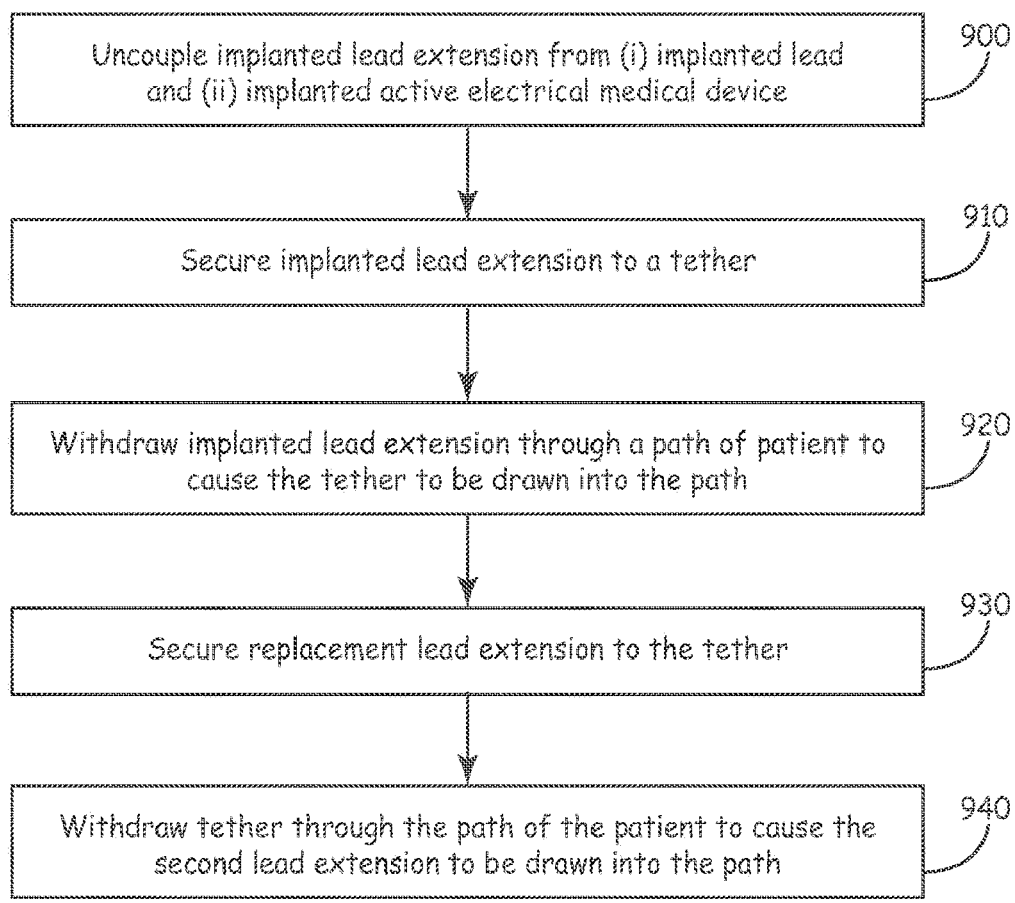

Flow diagrams depicting overviews of some of the methods described herein are presented in FIGS. 10-11. Referring now to FIG. 10, an embodiment of a method described herein for replacing a first implanted lead extension in a subject with a second lead extension includes uncoupling the first implanted lead extension from (i) an implanted lead and (ii) an implanted electrical medical device (800). The method further includes securing the second lead extension relative to the first implanted lead extension (810), and withdrawing the first implanted lead extension from the patient through a path to cause the second lead extension to be drawn into the tunneled path while the first implanted lead extension is withdrawn (820).

As shown in FIG. 11, a method for replacing a first implanted lead extension in a subject with a second lead extension may include uncoupling the first implanted lead extension from (i) an implanted lead and (ii) an implanted electrical medical device (900); securing first lead extension to a tether (910); and withdrawing the first implanted lead extension from the patient through a path to cause the tether to be drawn into the tunneled path in a first direction while the first implanted lead extension is withdrawn (920). The method may further include securing the second lead extension to the tether (930), and withdrawing the tether from the patient through the path in a second direction generally opposite to the first direction to cause the second lead extension to be drawn into the tunneled path in a first direction while first implanted lead extension is withdrawn (940).

The tether devices described herein may be made from any suitable material or combination of materials. For example, the elongate bodies of the tethers, which may be wires, cords, tubes or the like, may be made from metals such as stainless steel or titanium or hard plastics. Similarly, the receptacles and tapered elements, when present, may also be made from any suitable metal or hard plastic material.

Thus, embodiments of METHOD AND APPARATUS FOR REPLACING LEAD EXTENSION WITHOUT TUNNELING are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A tether comprising:
   a receptacle configured to receive and secure, but not electrically couple to, a free end portion of a first lead extension, the receptacle having a tapered front portion and a generally opposing back portion such that the free end portion of the first lead extension is configured to be received into a front face of the receptacle;
   an elongate body comprising a first end at the back portion of the receptacle and a free end opposing the first end, wherein the elongate body extends from the first end at the back portion of the receptacle to the free end,
   wherein the free end is configured to be received and secured in another receptacle of a second lead extension; and
   a tapered element disposed about the elongate body at a distance from the receptacle when the first end of the elongate body is at the back portion of the receptacle, the tapered element having a receptacle-facing end and a free end-facing end, the receptacle-facing end having a smaller diametric dimension than the free end-facing end.

2. The tether of claim 1, wherein the receptacle comprises a body having a longitudinal axis, the body defining a lumen configured to receive the free end portion of the first lead extension.

3. The tether of claim 2, wherein the receptacle comprises a clamp within the lumen for securing the free end portion of the first lead extension in the lumen.

4. The tether of claim 3, wherein the clamp comprises a resiliently deflectable arm having teeth configured to engage the free end portion of the first lead extension.

5. The tether of claim 2, wherein the lumen defined by the body of the receptacle extends from the tapered front portion of the receptacle toward, but not through, the generally opposing back portion of the receptacle.

6. The tether of claim 1, wherein the tapered element has a portion having a larger diametric dimension and the larger diametric dimension is larger than a diametric dimension of the elongate body.

7. The tether of claim 1, wherein the front face of the receptacle is a closed circle comprising an aperture defining an opening of the receptacle.

8. The tether of claim 1, wherein the elongate body comprises the free end while extending from the back portion of the receptacle.

9. The tether of claim 1, wherein the tapered element has a frustoconical shape.

* * * * *